United States Patent
Ryan et al.

(10) Patent No.: US 9,861,506 B2
(45) Date of Patent: Jan. 9, 2018

(54) REDUCED WIRE PROFILE STENT

(71) Applicant: Cook Medical Technologies LLC, Bloomington, IN (US)

(72) Inventors: Michael Ryan, Limerick (IE); James M. Carlson, Warsaw, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/082,434

(22) Filed: Mar. 28, 2016

(65) Prior Publication Data

US 2016/0206453 A1 Jul. 21, 2016

Related U.S. Application Data

(63) Continuation of application No. 13/644,255, filed on Oct. 3, 2012, now Pat. No. 9,320,623.

(60) Provisional application No. 61/543,166, filed on Oct. 4, 2011.

(51) Int. Cl.
   *C25F 3/16* (2006.01)
   *A61F 2/90* (2013.01)
   *A61F 2/86* (2013.01)

(52) U.S. Cl.
   CPC .............. *A61F 2/90* (2013.01); *A61F 2/86* (2013.01); *C25F 3/16* (2013.01); *A61F 2220/0008* (2013.01); *A61F 2220/0016* (2013.01); *A61F 2230/0078* (2013.01); *A61F 2240/001* (2013.01); *A61F 2250/0036* (2013.01); *A61F 2250/0039* (2013.01)

(58) Field of Classification Search
   CPC ................................ C25F 3/16–3/26
   See application file for complete search history.

(56) References Cited

U.S. PATENT DOCUMENTS

| | | |
|---|---|---|
| 5,938,697 A | 8/1999 | Killion et al. |
| 6,325,825 B1 | 12/2001 | Kula et al. |
| 6,413,272 B1 | 7/2002 | Igaki |
| 6,616,688 B2 | 9/2003 | Von Oepen |
| 6,776,022 B2 | 8/2004 | Kula et al. |
| 6,796,997 B1 | 9/2004 | Penn et al. |
| 6,840,958 B2 | 1/2005 | Nunez et al. |
| 6,994,724 B2 | 2/2006 | Schmitt |
| 7,070,617 B2 | 7/2006 | Kula et al. |
| 7,547,321 B2 | 6/2009 | Silvestri et al. |
| 7,815,591 B2 | 10/2010 | Levine et al. |
| 2005/0049682 A1 | 3/2005 | Leanna et al. |

(Continued)

FOREIGN PATENT DOCUMENTS

| | | | |
|---|---|---|---|
| WO | WO 2005/011527 | 2/2005 | |
| WO | WO 2012/082440 A1 | 6/2012 | |
| WO | WO 2012087301 A1 * | 6/2012 | ............. A61F 2/852 |

OTHER PUBLICATIONS

Search Report dated Feb. 5, 2013 for co-pending PCT Patent Application No. PCT/US2012/058527.

(Continued)

*Primary Examiner* — Nicholas A Smith
(74) *Attorney, Agent, or Firm* — Brinks Gilson & Lione

(57) ABSTRACT

Methods and apparatuses of stents with likely reduced rates of tissue perforation are provided. Some embodiments include reducing the profile of a portion of the stent using a wire profile reduction electropolishing bath and/or other wire profile reduction means.

9 Claims, 7 Drawing Sheets

(56) References Cited

U.S. PATENT DOCUMENTS

| | | |
|---|---|---|
| 2005/0256563 A1 | 11/2005 | Clerc et al. |
| 2007/0150051 A1 | 6/2007 | Arnault de la Mendardiere et al. |
| 2007/0179590 A1 | 8/2007 | Lu et al. |
| 2008/0208322 A1 | 8/2008 | Sandhu |
| 2011/0054589 A1 | 3/2011 | Bashiri et al. |
| 2011/0214785 A1* | 9/2011 | Buckman, Jr. ......... B21D 31/00 148/237 |
| 2011/0265908 A1 | 11/2011 | Clerc et al. |
| 2012/0083871 A1 | 4/2012 | Ryan |
| 2012/0259404 A1 | 10/2012 | Tieu et al. |
| 2012/0310319 A1 | 12/2012 | Tieu et al. |

OTHER PUBLICATIONS

Official Action for corresponding EP Application No. 12 783 421.6, 6p, dated Oct. 4, 2017.

* cited by examiner

REDUCED WIRE PROFILE STENT

RELATED APPLICATIONS

This application is a continuation of U.S. patent application Ser. No. 13/644,255, filed Oct. 3, 2012, which claims the benefit of U.S. Provisional Application No. 61/543,166, filed on Oct. 4, 2011, the disclosures of which are incorporated herein by reference in their entireties.

TECHNICAL FIELD

The present invention relates to medical devices and more specifically, stents.

BACKGROUND

Stents are medical devices commonly used to maintain patency of body vessels, such as those of the vascular and gastrointestinal systems. Stents are often delivered via a minimally invasive procedure and thereafter expanded to contact and support the inner wall of the targeted vessel. In general, most stents include a tubular shaped support structure having a plurality of interstices configured to facilitate compression and expansion of the stent.

Many stents include proximal and distal flanges or flared ends to prevent stent migration subsequent to implantation. Flanges or flares are typically set to a larger expanded diameter relative to the stent central portion and may exert a higher radial force per unit area against the vessel wall, thereby securing the stent in position. One problem with these features, however, is that the flanges or flares can damage the vessel wall if they are excessively rigid. Specifically, the crowns at the end of a flange or flare can cause perforations as the luminal wall engages the stent during peristalsis. The resulting tissue perforations may be painful and can lead to more serious complications including infection, hemorrhage, and possibly death.

BRIEF SUMMARY

In a first aspect, a stent is provided, including a wire configured into a tubular body including a proximal tube portion, a distal tube portion, a central tube portion disposed between the proximal tube portion and the distal tube portion, and a lumen extending between the proximal tube portion and the distal tube portion; wherein the wire includes a first profile and a second profile, wherein the second profile is different from the first profile.

In a second aspect, a method of manufacturing a reduced wire profile stent is provided, including bathing a first portion of a wire stent in a first wire profile reduction solution; and applying a first electropolishing voltage to the first wire profile reduction solution bath to reduce the profile of the first portion of the wire stent.

In a third aspect, a method of manufacturing a changed profile wire stent is provided, including subjecting a first portion of a wire stent to a wire profile reduction means to change the profile of the first portion of the wire stent.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

DETAILED DESCRIPTION OF PRESENTLY PREFERRED EMBODIMENTS

Figure 1:
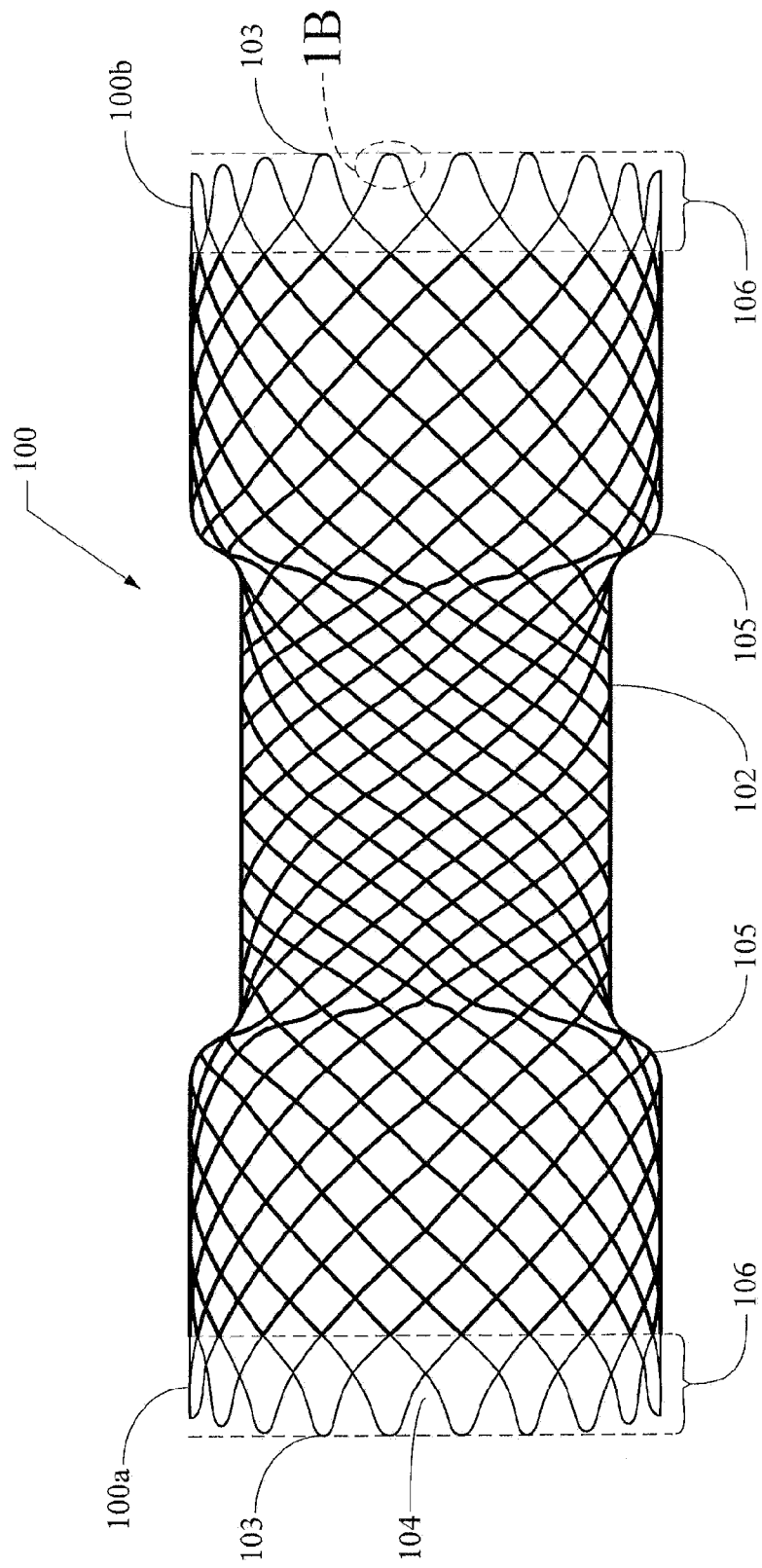
FIG. 1 illustrates a side view of an exemplary reduced wire diameter stent.

The exemplary embodiments illustrated provide the discovery of methods and apparatuses for manufacturing stents which may have reduced rates of tissue perforation achieved by various apparatuses and methods, including but not limited to, reducing the wire profile of one or more portions of the stent such as by subjecting it to a wire profile reduction electropolishing bath and/or other wire profile reduction means.

The present invention is not limited to those embodiments described herein, but rather, the disclosure includes all equivalents including those of different shapes, sizes, and configurations, including but not limited to, other types of stents. The devices and methods may be used in any field benefiting from a stent. Additionally, the devices and methods are not limited to being used with human beings, others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are described below, although apparatuses, methods, and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

A more detailed description of the embodiments will now be given with reference to FIGS. 1-6. Throughout the disclosure, like reference numerals and letters refer to like elements. The present disclosure is not limited to the embodiments illustrated; to the contrary, the present disclosure specifically contemplates other embodiments not illustrated but intended to be included in the claims.

When in a body, stents are often subjected to tortuous conditions, especially in bodily areas wherein peristaltic motion is present or when the stent is subjected to a curved orientation, such as when disposed within the colon or duodenum. When in such a position, the radial force exerted by the stent onto the surrounding tissue may cause such tissue to perforate, thereby injuring or causing death to the patient. One advantage from the embodiments disclosed herein and equivalents thereto is that the stent is able to better conform to the tissue and is better able to adapt to the tissue environment while maintaining good radial force to maintain an open pathway. Another advantage includes, but is not limited to, that the embodiments may aid in the reduction of hyperplasia in that the radial force exerted from the stent may be tailored to the surrounding tissue. Such benefits and other benefits are achievable through various apparatuses and methods described herein and equivalents thereto.

For example, FIG. 1 illustrates a side view of exemplary reduced wire diameter stent 100 having proximal portion 100a, distal portion 100b, and a generally cylindrical tubular shaped stent body 102 having lumen 104 extending throughout. Stent 100 is preferably made from a shape memory alloy, such as nitinol, although other materials are contemplated, including but not limited to FeMnSi and FeNiCo(Al, Ti)Ta with or without B, Fe₃Pt.

At proximal portion 100a and distal portion 100b of stent 100 are flanges 105 terminating in crowns 103. Stent 100 comprises a single wire wound in a helical pattern forming a cylindrical tubular shape; other embodiments of wire stents are contemplated, including but not limited to, those fabricated from two or more wires having helical or other configurations. After stent 100 is fabricated, the diameter of wire first portion 106 is reduced by about 50% (other amounts are contemplated) thereby making proximal portion 100a and distal portion 100b of stent 100 more flexible and less traumatic to tissue, and thus, less likely to perforate tissue.

Figure 1A:
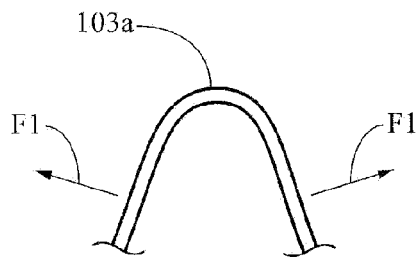
FIG. 1A illustrates a side view of an exemplary wire crown prior to wire diameter reduction.
Figure 1B:
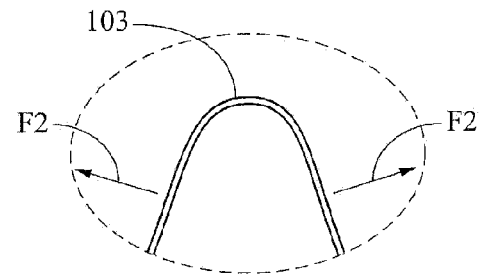
FIG. 1B illustrates a side view of an exemplary wire crown after wire diameter reduction at the view 1B illustrated in FIG. 1.

FIG. 1A illustrates a side view of exemplary wire crown 103a prior to wire diameter reduction, and FIG. 1B illustrates a side view of exemplary wire crown 103 after wire diameter reduction at the view 1B illustrated in FIG. 1. As is illustrated in FIG. 1A, the diameter of stent wire at crown portion 103a prior to having the wire diameter reduced is 50% larger than is reduced wire crown portion 103 illustrated in FIG. 1B. Accordingly, force F1 (illustrated in FIG. 1A) exerted from the stent prior to wire diameter reduction is greater than force F2 (illustrated in FIG. 1B) exerted after wire diameter reduction.

The flexural stiffness (K) of a component is generally defined by:

$$EI\frac{dy}{dx} = \int_0^x M(x)dx + C_1$$

(hereafter, "Equation 1"), where E=materials Young's modulus (Pascal); I=second moment of inertia (m⁴); y=transverse displacement of a beam at x; and M(x)=bending moment at x. The flexural stiffness has SI units of Pa.m⁴. As further explained herein, a wire beam may have any profile shape and is not limited to having a circular cross-sectional profile. However, for explanatory purposes, a circular cross-sectional profile will be considered only for these next equations. Also assumed only for these next equations is that the materials are constant such that the stent is fabricated and then electropolished (although as further described, other wire profile reduction means are contemplated so as to produce a different wire profile from the initial wire profile). Furthermore, it is assumed only for these next equations that the x and y values are identical, such that the $X_{pre}$ and $Y_{pre}$ values=$X_{post}$ and $Y_{post}$ respectively, wherein "pre" and "post" refer to pre-wire reduction and post-wire reduction. Making these assumptions, Equation 1 simplifies to K=EI (hereafter "Equation 2"). The second moment of inertia (for a circular cross-section) is defined by $$I = \frac{\pi D^4}{64}$$

(hereafter "Equation 3"), where D=diameter of circular cross-section (m). Consequently, Equation 2 can be rewritten as $$K = \frac{E\pi D^4}{64}$$

(hereafter "Equation 4"). Eliminating the constants in this equation, based on the assumptions cited above, the flexural stiffness is dictated by D⁴. Thus, K∝D⁴ (hereafter "Equation 5"). Therefore a small change in diameter will have a large change in flexural stiffness.

The one or more wires comprising stent embodiments and equivalents thereto are not limited to having a circular cross-sectional profile; other profiles are contemplated, including but not limited to, a rectangular cross-section profile, square cross-sectional profile, oval cross-sectional profile, triangular cross-section profile, an irregular (or non-uniform) cross-sectional profile, or some combination thereof. Accordingly, as used herein, a "profile" of the one or more wires may be any means of defining a diameter, length, width, height, or other measurement of a wire, such as is appropriate for the specific shape of the wire whether it be a circle, oval, rectangle, square, or other shape. Thus, although some embodiments illustrate a reduced wire diameter, the embodiments and methods are not limited to circular cross-sectional profile wires; instead, they include, but are not limited to, one or more wires having any profile shape whether that cross-sectional length, height, width, or other portion be described using a term other than "diameter." Reducing the profile of the wire such that it is different from its initial wire profile may be achieved through numerous means, including but not limited to, reducing the diameter of a round wire and/or reducing the cross section of a flat wire or changing the shape of the wire. For example, it is contemplated that the shape of round wire may be altered into more rectangular shape or other desired shape. A change of the wire profile may be achieved by electropolishing, immersion into an acid, sanding/grinding, or some combination thereof.

Accordingly, because the diameter of wire first portion 106 has been changed, the radial force is also reduced. However because stent body 102 maintains its initial wire diameter, the radial force in that portion is not reduced. Accordingly, reduced wire diameter stent 100 performs like known wire stents but will likely reduce the incidence of tissue perforation caused by typical flanges and/or crowns perforating tissue due to the typically high radial force exerted therefrom.

Figure 1C:
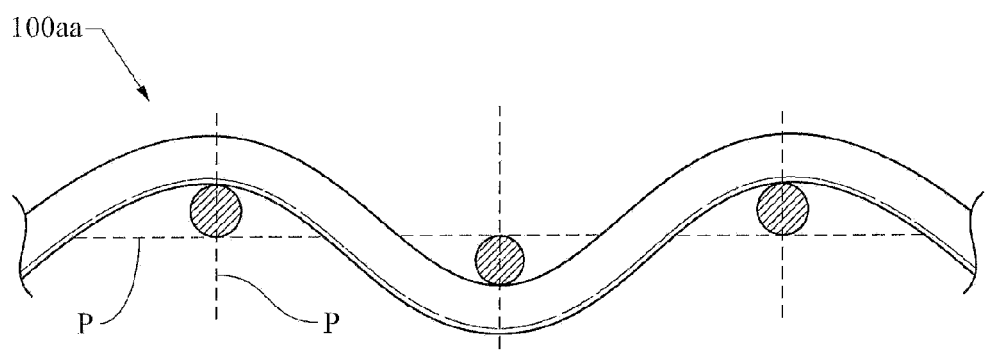
FIG. 1C illustrates a front cross-sectional view of an exemplary proximal end of a stent prior to wire profile reduction.
Figure 1D:
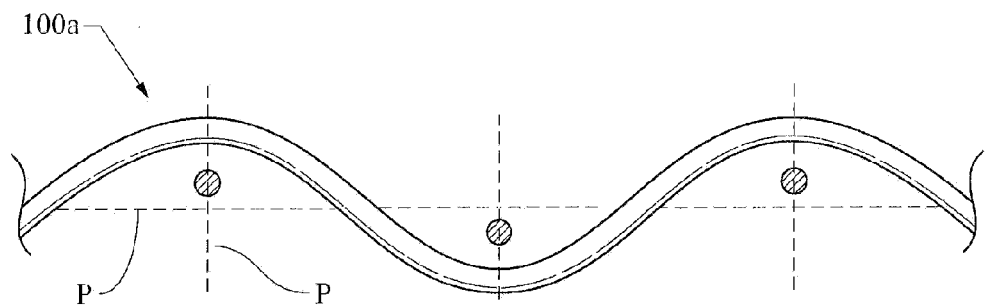
FIG. 1D illustrates a front cross-sectional view of an exemplary proximal end of the exemplary stent illustrated in FIG. 1 after wire diameter reduction.

FIG. 1C illustrates a front cross-sectional view of an exemplary proximal end 100aa of a stent prior to wire profile reduction, and FIG. 1D illustrates a front cross-sectional view of exemplary proximal end 100a of a stent after wire diameter reduction.

Referring to FIGS. 1C-1D, wires remain situated within the same plane P before wire diameter reduction (illustrated in FIG. 1C) and after wire diameter reduction (illustrated in FIG. 1D). Moreover, as compared with proximal portion 100aa (illustrated in FIG. 1C), the wire tension (illustrated in FIG. 1D) is reduced thereby resulting in a more flexible proximal portion 100a (illustrated in FIG. 1D) than proximal portion 100aa (illustrated in FIG. 1C).

Figure 2:
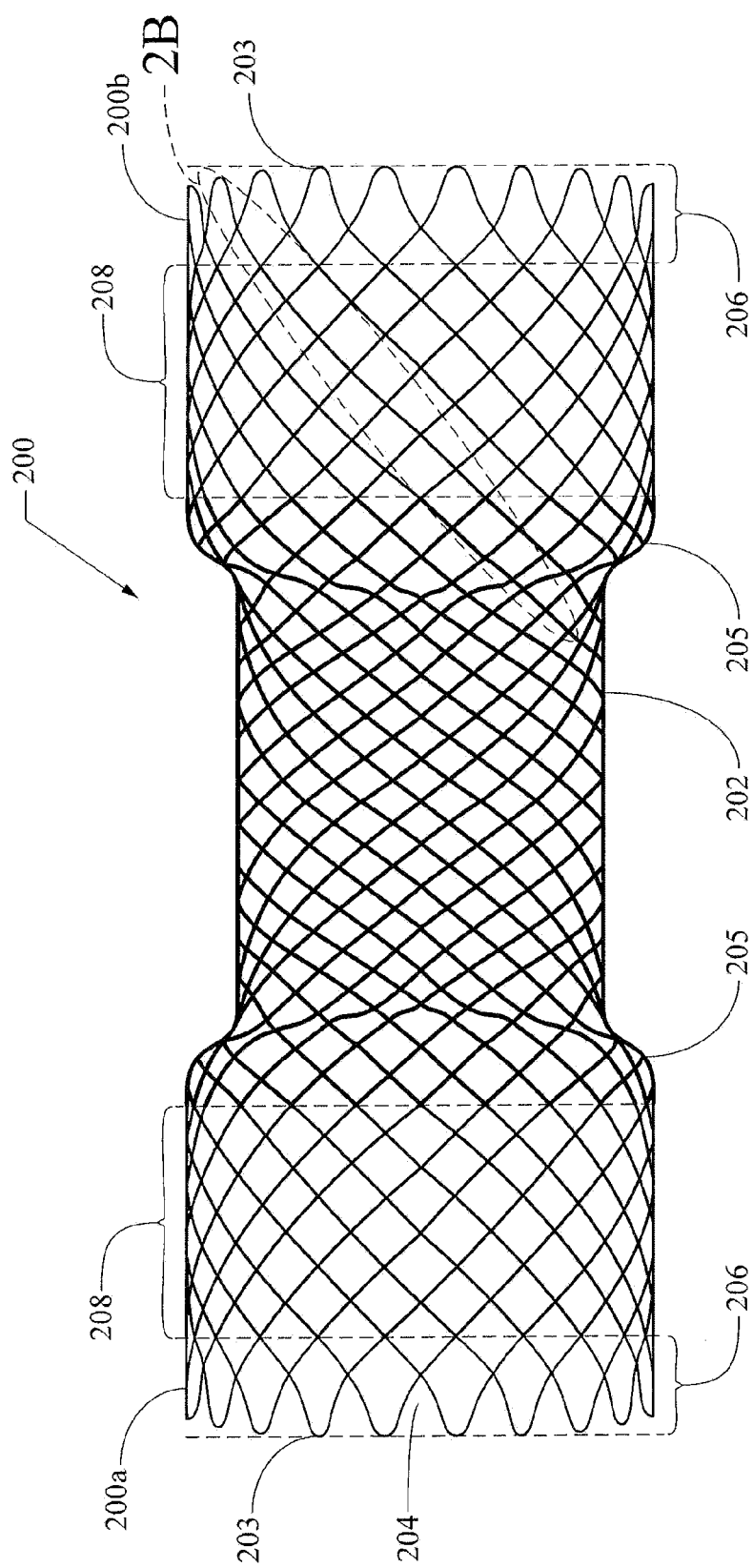
FIG. 2 illustrates a side view of an exemplary reduced wire diameter stent.
Figure 2A:
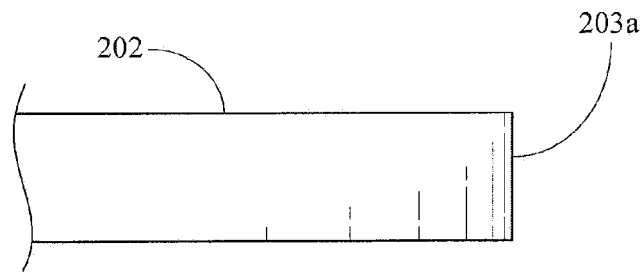
FIG. 2A illustrates a side view of an exemplary stent wire prior to wire diameter reduction.
Figure 2B:
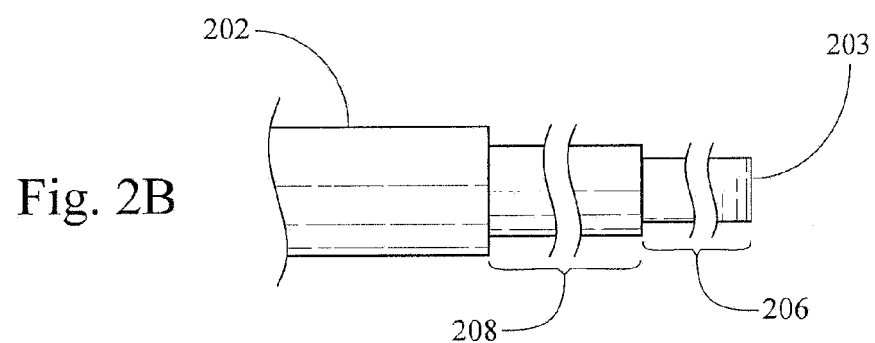
FIG. 2B illustrates a side view of the exemplary stent wire after wire diameter reduction at the view 2B illustrated in FIG. 2.

FIG. 2 illustrates a side view of exemplary reduced wire diameter stent 200 having proximal portion 200a, distal portion 200b, and a generally cylindrical tubular shaped stent body 202 having lumen 204 extending throughout. FIG. 2A illustrates a side view of exemplary stent wire crown portion 203a prior to wire diameter reduction, and FIG. 2B illustrates a side view of stent wire crown portion 203 after wire diameter reduction at the view 2B illustrated in FIG. 2. Referring to FIGS. 2-2B, at proximal portion 200a and distal portion 200b of stent 200 are flanges 205 terminating in crowns 203. Stent 200 comprises a single wire wound in a helical pattern; other embodiments of wire stents are contemplated, including but not limited to, those fabricated from two or more wires having helical or other configurations. After stent 200 is fabricated, the diameter of wire first portion 206 is reduced by a first reduction amount, and the diameter of wire second portion 208 is reduced by a second reduction amount. For example, the diameter of wire first portion 206 is reduced by about 50%, and the diameter of wire second portion 208 is reduced by about 30%. Other reduction amounts are contemplated. Because wire first portion 206 and wire second portion 208 are reduced diameter wires, proximal portion 200a and distal portion 200b of stent 200 are more flexible and less traumatic to tissue, and thus, less likely to perforate tissue. Accordingly, because the diameter of wire first portion 206 has been reduced by an amount greater than wire second portion 208, the radial force at wire first portion 206 is less than at wire second portion 208, and is less than at stent body 202. Because stent body 202 maintains its initial wire diameter, the radial force in that portion is not reduced. Accordingly, reduced wire diameter stent 200 performs like known wire stents but will likely reduce the incidence of tissue perforation caused by typical flanges and/or crowns perforating tissue due to the typically high radial force exerted therefrom.

Figure 3:
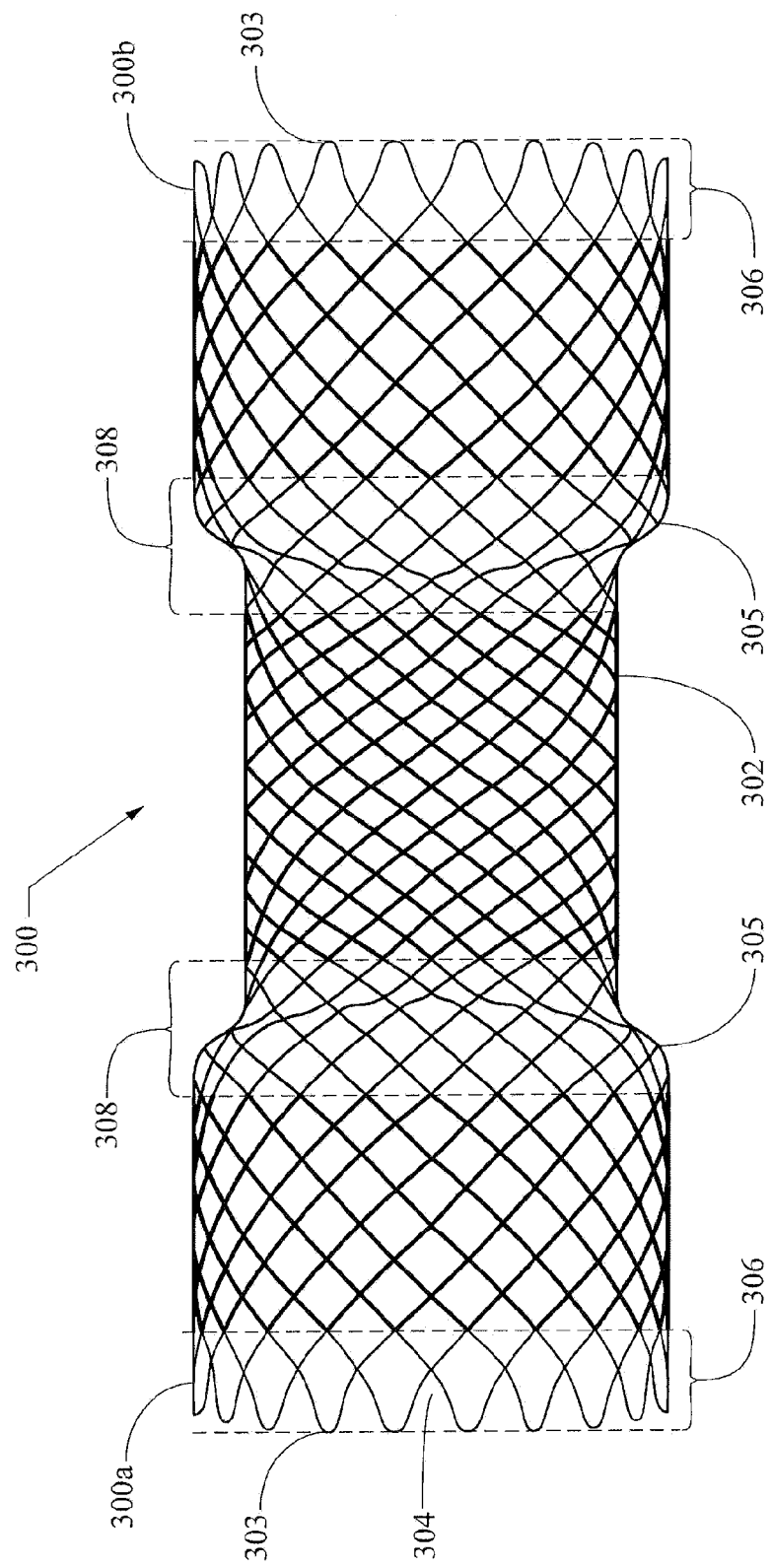
FIG. 3 illustrates a side view of an exemplary reduced wire diameter stent.

FIG. 3 illustrates a side view of exemplary reduced wire diameter stent 300 having proximal portion 300a, distal portion 300b, and a generally cylindrical tubular shaped stent body 302 having lumen 304 extending throughout. At proximal portion 300a and distal portion 300b of stent 300 are flanges 305 terminating in crowns 303. Stent 300 comprises a single wire wound in a helical pattern; other embodiments of wire stents are contemplated, including but not limited to, those fabricated from two or more wires having helical or other configurations. After stent 300 is fabricated, the diameter of wire first portion 306 is reduced by a first reduction amount, and the diameter of wire second portion 308 is reduced by a second reduction amount. For example, the diameter of wire first portion 306 is reduced by about 50%, and the diameter of wire second portion 308 is reduced by about 30%. The reductions in diameters for each portion may be the same or different, and other reduction amounts are contemplated. Because wire first portion 306 and wire second portion 308 are reduced diameter wires, they are more flexible and less traumatic to tissue. Since a portion of stent body 302 maintains its initial wire diameter, the radial force in that portion is not reduced. Accordingly, reduced wire diameter stent 300 performs like known wire stents but will likely reduce the incidence of tissue perforation caused by typical flanges and/or crowns perforating tissue due to the typically high radial force exerted therefrom and by permitting body portion of stent to be more flexible at wire second portion 308.

Figure 4:
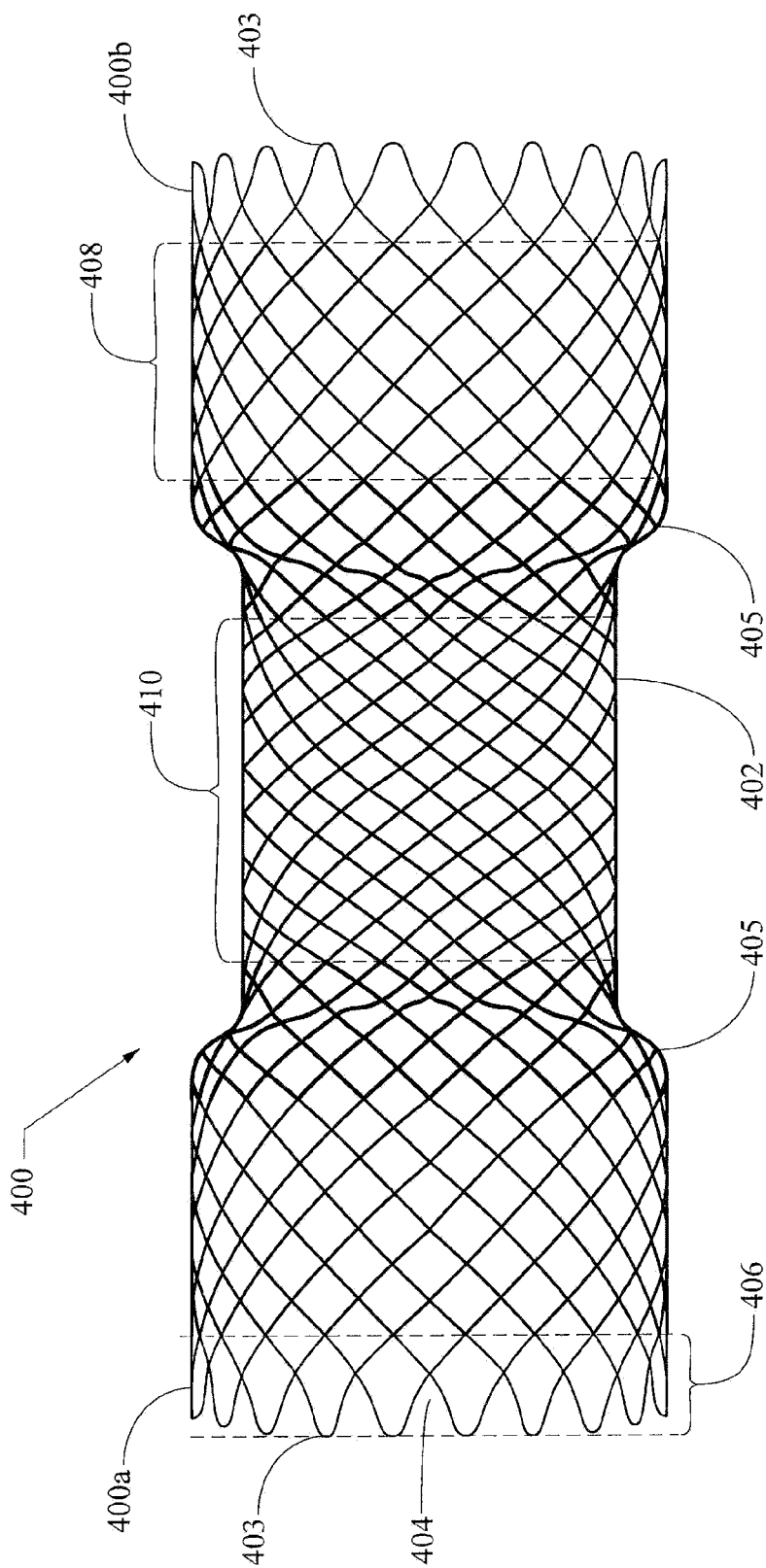
FIG. 4 illustrates a side view of an exemplary reduced wire diameter stent.

FIG. 4 illustrates a side view of exemplary reduced wire diameter stent 400 having proximal portion 400a, distal portion 400b, and a generally cylindrical tubular shaped stent body 402 having lumen 404 extending throughout. At proximal portion 400a and distal portion 400b of stent 400 are flanges 405 terminating in crowns 403. Stent 400 comprises a single wire wound in a helical pattern; other embodiments of wire stents are contemplated, including but not limited to, those fabricated from two or more wires having helical or other configurations. After stent 400 is fabricated, the diameter of wire first portion 406 is reduced by a first reduction amount, the diameter of wire second portion 408 is reduced by a second reduction amount, and the diameter of wire third portion 410 is reduced by a third reduction amount. For example, the diameter of wire first portion 406 is reduced by about 50%, the diameter of wire second portion 408 is reduced by about 30%, and the diameter of wire third portion 410 is reduced by about 10%. The reductions in diameters for each portion may be the same or different, and other reduction amounts are contemplated. Because wire first portion 406, wire second portion 408, and wire third portion 410 are reduced diameter wires, they are more flexible and less traumatic to tissue. Because a portion of stent body 402 maintains its initial wire diameter, the radial force in that portion is not reduced. Accordingly, reduced wire diameter stent 400 performs like known wire stents but will likely reduce the incidence of tissue perforation caused by typical flanges and/or crowns perforating tissue due to the typically high radial force exerted therefrom and by permitting body portion of stent to be more flexible at wire third portion 410.

Figure 5:
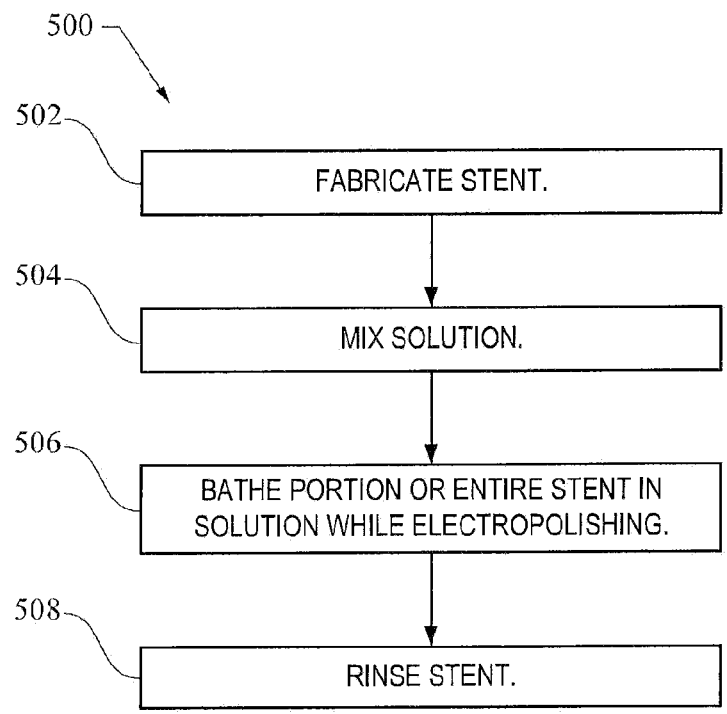
FIG. 5 illustrates an exemplary method of manufacturing a reduced wire diameter stent.

FIG. 5 illustrates exemplary method of manufacturing a reduced wire profile stent 500, such as those illustrated in FIGS. 1-4. At block 502, a wire stent is fabricated. At block 504, a wire profile reduction solution is mixed and is preferably made to an ideal temperature. At block 506, all or a portion of the stent is bathed in the solution while being electropolished to the desired wire profile by applying an electropolishing voltage to the wire profile reduction solution. At block 508, the stent is rinsed of the wire profile reduction solution. It is contemplated that an electropolishing voltage need not be applied, such as in the case of, for example, bathing stent in certain acid baths.

Figure 6:
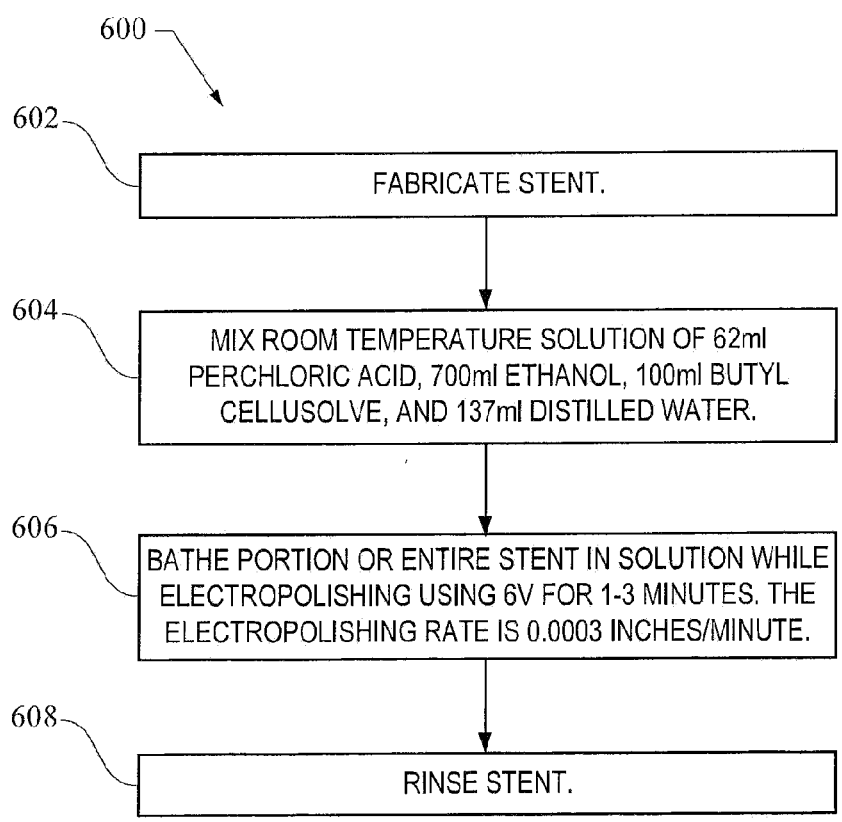
FIG. 6 illustrates an exemplary method of manufacturing a reduced wire diameter stent.

FIG. 6 illustrates exemplary method of manufacturing a reduced wire profile stent 600, such as those illustrated in FIGS. 1-4. At block 602, a wire stent is fabricated. At block 604, a wire profile reduction solution of 62 ml perchloric acid, 700 ml ethanol, 100 ml butyl cellusolve, and 137 ml distilled water is mixed and brought to room temperature. At block 606, all or a portion of the stent is bathed in the solution while being electropolished using 6 volts for 1-3 minutes such that the wire profile is reduced to the desired amount. Using this method, a typical stent's wire diameter having a circular cross-sectional profile (other profile configurations are contemplated) is reduced at a rate of about 0.0003 inches per minute.

At block 608, the stent is then rinsed of the wire profile reduction solution by, for example, rinsing the stent in deionized water for about one minute. The stent is then neutralized in a mild basic solution, including but not limited to, aqueous sodium bi-carbonate, ammonium hydroxide, or sodium hydroxide, for about 1-3 minutes. Thereafter, the stent is rinsed in deionized water for about one minute. It is preferred that rinsing of the stent occurs using ultrasonic means and be done at room temperature. Other rinsing materials, agents, and methods are contemplated. Optionally, a coating or membrane can be applied to all or a portion of the stent.

Additional means and methods for reducing the wire profile of a stent or portion thereof such that the wire profile is different from its initial wire profile are illustrated in Table 1, below, such that the wire profile reduction solution is mixed and brought to a preferred temperature, and all or a portion of the stent is bathed and/or electropolished until the wire profile is reduced to a certain shape, measurement, or by a certain percentage. The wire profile reduction solution is then rinsed from the stent, by for example, rinsing the stent in deionized water for about one minute. The stent is then neutralized in a mild basic solution, including but not limited to, aqueous sodium bi-carbonate, ammonium hydroxide, or sodium hydroxide, for about 1-3 minutes. Thereafter, the stent is rinsed in deionized water for about one minute. It is preferred that rinsing of the stent occurs using ultrasonic means and be done at room temperature. Other rinsing materials, agents, and methods are contemplated The wire diameter reduction rates illustrated in FIG. 5 and Table 1 assume a round wire stent fabricated from nitinol, but other materials are contemplated which may alter the wire diameter reduction rate. Moreover, other wire profile reduction solutions are contemplated, including those for use with materials other than nitinol. The wire profile reduction solutions contemplated are not limited to those illustrated in FIG. 5 and Table 1. For example, if the stent comprises ferrous shape memory alloys, then it is preferred, although not required, that the wire profile reduction solution comprise a mixture of sulfuric—phosphoric acids, such as Electro-Glo™ (available from Electro-Glo Distribution Inc., LaSalle, Ill.).

TABLE 1

| Wire Profile Reduction Solution | Approximate Solution Temperature | Approximate Duration of Electropolishing Bath | Approximate Wire Diameter Reduction Rate (Inches/Min) |
| --- | --- | --- | --- |
| 60 ml perchloric acid, 590 ml methanol, and 350 ml butyl cellusolve. | Room temperature. | 6 V for about 1-3 minutes. | About 0.0003. |
| 21 ml perchloric acid (70%) and 79 ml acetic acid. | Room temperature. | 6 V for about 1-3 minutes. | About 0.0003. |
| 6 ml perchloric acid (70%) and 94 ml acetic acid. | Room temperature. | 6 V for about 1-3 minutes. | About 0.0003. |
| Pickle stent for 6 minutes in 2 ml hydrofluoric acid and 40 ml nitric acid, and then bathe stent in 5 ml perchloric acid (70%) and 100 ml acetic acid. | Room temperature. | 20 V 0.15 amps for about 1.5-2 minutes. | About 0.0003. |
| 30 ml nitric acid, 10 ml sulphuric acid, 10 ml orthophosphoric acid, and 50 ml glacial acetic acid. | Room temperature. | 6 V for about 3-5 minutes. | About 0.0005. |
| 10 ml nitric acid, 5 ml acetic acid, and 85 ml distilled water. | Room temperature. | 6 V for about 3-5 minutes. | About 0.0005. |
| 50 ml nitric acid and 50 ml acetic acid. | Room temperature. | 6 V for about 3-5 minutes. | About 0.0005. |

TABLE 1-continued

| Wire Profile Reduction Solution | Approximate Solution Temperature | Approximate Duration of Electropolishing Bath | Approximate Wire Diameter Reduction Rate (Inches/Min) |
| --- | --- | --- | --- |
| 33 ml nitric acid and 67 ml methanol. | Cool solution to −30° Celsius. | 5.5 V with 0.1 A/cm$^2$ for about 3-5 minutes. | About 0.0003. |
| 30 ml nitric acid and 70 ml methanol. | Cool solution to −30° Celsius. | 15 V for about 1 minute. | About 0.0003. |
| 0.01-1 gram chromium trioxide and 100 ml hydrochloric acid. | Room temperature. | 6 V for about 3-5 minutes. | About 0.0005. |
| 10 ml hydrofluoric acid, 25 ml nitric acid, and 150 ml distilled water. | Room temperature. | 6 V for about 1-3 minutes. | About 0.0003. |
| 5 ml hydrofluoric acid, 10 ml nitric acid, and 100 ml glycerin. | Room temperature. | 6 V for about 1-3 minutes. | About 0.0005. |

Care is to be taken when using any of the wire profile reduction solutions, especially when using the wire profile reduction solutions containing acid, so as not to burn oneself or unintended portions of the stent. Wire profile reduction solutions not containing perchloric acid or hydrofluoric acid are generally less aggressive than those containing perchloric acid or hydrofluoric acid, but such solutions generally reduce the wire diameter at a slower rate.

In some embodiments, only the end portions of the stent are each subjected to the wire profile reduction electropolishing bath. For example, as illustrated in FIG. 1, wire first portions 106 are each subjected to the wire profile reduction electropolishing bath to reduce the wire diameters by about 50%.

In some embodiments, one or more portions of the stent will be subjected to one or more wire profile reduction electropolishing baths until the desired reduced wire diameters are achieved. For example, as illustrated in FIG. 2, wire first portion 206 and wire second portion 208 are subjected to the wire profile reduction electropolishing bath to reduce the wire diameter by about 30%. Thereafter, wire first portion 206 is further subjected to the wire profile reduction electropolishing bath to further reduce its wire diameter by about another 20%, such that wire first portion 206 has a final reduced wire diameter of about 50% from the initial wire diameter.

In some embodiments, a portion of the stent can be masked such that only certain portions of the stent are subjected to the wire profile reduction electropolishing bath at certain times. For example, as illustrated in FIG. 3, the portion of stent not to have a reduced wire diameter is masked while stent 300 is subjected to the wire profile reduction electropolishing bath until the diameter of wire first portion 306 and wire second portion 308 are reduced by about 30%. Thereafter, all but wire first portion 306 is masked while stent 300 is subjected to the wire profile reduction electropolishing bath until the diameter of wire first portion 306 is reduced by about 20% to a total of about a 50% reduction from the initial wire diameter.

For example, as illustrated in FIG. 4, all but wire third portion 410 is masked while stent 400 is subjected to the wire profile reduction electropolishing bath until the diameter of wire third portion 410 is reduced by about 10%. Thereafter, all but wire second portion 408 is masked while stent 400 is subjected to the wire profile reduction electropolishing bath until the diameter of wire second portion 408 is reduced by about 30%. Thereafter, all but wire first portion 406 is masked while stent 400 is subjected to the wire profile reduction electropolishing bath until the diameter of wire first portion 406 is reduced by about 50%.

In some embodiments, stents and equivalents thereof have portions of a wire outer surface or wire inner surface masked such that an irregular cross-section profile is created and/or the shape of the wire is altered when subjected to the wire profile reduction electropolishing bath.

In some embodiments, two or more stents may be subjected to the wire profile reduction electropolishing bath simultaneously to increase the speed at which reduced wire profile stents may be manufactured. In some embodiments, the wire profile reduction solution amount will be increased, preferably maintaining the ratio of each portion of the solution (e.g., doubling, tripling, etc.), to accommodate two or more stents to be subjected to the wire profile reduction electropolishing bath. In some embodiments, the amount of time two or more stents are subjected to the wire profile reduction electropolishing bath will be altered, such as by increasing the exposure time, so as to accommodate two or more stents to be bathed simultaneously.

Other wire profile reduction means such that the wire profile is different from its initial wire profile are contemplated in addition to use of a wire profile reduction electropolishing bath. Such means may be used separate or in conjunction with one another. For example, wire profile reduction means include, but are not limited to, subjecting one or more wires or portions thereof to a wire profile reduction electropolishing bath, swaging one or more wires or portions thereof, crimping one or more wires or portions thereof, grinding one or more wires or portions thereof, and bathing one or more wires or portions thereof in acid or other chemical(s) such that the one or more profiles of the wires or portions thereof is reduced or the wire configuration is otherwise altered such that the wire is more flexible and exhibits a reduced moment of inertia.

As can be seen, embodiments of reduced wire profile stents may have one or more portions of its body and/or flanges reduced by one or more wire profile reduction amounts. Although FIG. 1, for example, illustrates wire first portions 106 having reduced wire diameters on both flanges 105, it is contemplated that only a single portion of stent 100 include a reduced profile wire. In other words, the reduced profile wire portion need not be included on both the proximal and distal portions of the stent and the resulting stent need not be symmetrical.

In some embodiments, only the proximal portion (or portions thereof) of the stent will have a reduced profile wire. In some embodiments, only the distal portion (or portions thereof) of the stent will have a reduced profile wire. In some embodiments, only the middle stent body portion (or portions thereof) of the stent will have a reduced profile wire. In some embodiments, the stent will have a combination of reduced profile wire portions on various portions of the stent. In some embodiments, the reduced profile wire portions will be adjacent to each other. In some embodiments, the reduced profile wire portions will be separate from each other.

In some embodiments, the reduced profile wire portions will be reduced by the same amount. In some embodiments, the reduced profile wire portions will be reduced by different amounts. In some embodiments, the reduced profile wire portions will abruptly change from one profile size or configuration to another.

Figure 2C:
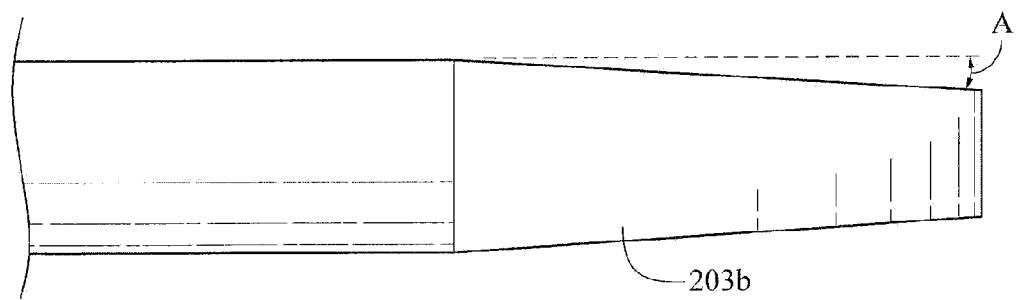
FIG. 2C illustrates a side view of an alternate stent wire after wire diameter reduction.

In some embodiments, the reduced profile wire portions will gradually change from one profile size or configuration to another, such as in a tapered reduction rate, as illustrated in FIG. 2C, wherein crown portion 203b has a reduced tapered wire diameter. Still referring to FIG. 2C, reduction angle A preferably is a shallow angle of about 0.1 degrees, 0.01-2 degrees, but other angles are contemplated depending upon the length of the taper and the desired wire profile. Means for achieving a tapered reduced wire profile configuration include, but are not limited to, a controlled slow withdrawal from the wire profile reduction electropolishing bath and/or other wire profile reduction means.

In some embodiments, the wire profile will be reduced by about 1%-50%. In some embodiments, the wire profile will be reduced by more than 50%, such as 70%, taking care not to reduce the wire profile by too high of an amount such that the wire will fail due to fatigue. For example, in some embodiments the wire profile will be reduced by from about 10% to about 75%. In other embodiments, the wire profile will be reduced by about 10-25%, about 25-40%, about 40-60%, or about 60-75%. In still other embodiments, the wire profile will be reduced by about 50%.

In some embodiments, the voltage applied to a wire profile reduction electropolishing bath will be the same or different from the voltage applied to other wire profile reduction electropolishing baths to reduce the wire diameter of one or more portions of a stent. In some embodiments, the wire profile reduction solutions used to reduce the wire diameter of one or more portions of the stent will be the same or different. In some embodiments, the amount of time portions of a stent are subjected to a wire profile reduction electropolishing bath will be the same or different.

In some embodiments, a stent is covered with a membrane. The membrane covering may be applied to a stent by any suitable method as is known in the art. For example, the membrane may be applied by spraying, dipping, painting, brushing, or padding. Generally, the membrane covering or coating has a thickness ranging from about 0.0025 mm to about 2.5 mm. The thickness of the membrane may be selected, for example, by controlling the number of dips or passes made during the application process. In one exemplary embodiment, a braided stent may be dipped in silicone liquid, removed, and thereafter cured. Preferably, the coating extends over the abluminal and luminal surfaces of the filaments, and also resides in the cells or interstices defined by the filament braid pattern. In certain embodiments, the coating may be selectively applied to the luminal or abluminal surfaces of the stent structure such that the coating residing within the cells is biased to the luminal or abluminal surface of the stent structure.

In some embodiments, after the membrane has been applied to the stent structure, "soft cells" may be created by manually removing a covering, such as silicone, from the selected cells with an appropriate tool. For example, devices such as needles and forceps may be used to remove membrane material from selected cells to create a desired pattern of soft cells. In an alternative embodiment, the soft cells in the stent pattern may fabricated by covering or shielding certain cells prior to application of the membrane coating. For example a segment of shrink wrap comprising polytetrafluoroethylene may be applied to a circumferential row of cells by placing a piece of the material at the desired location and thereafter heat shrinking in place. With the selected cells shielded, the membrane material may be applied and cured, and the shrink wrap thereafter removed. This procedure may minimize or eliminate the need for manual removal of silicone from selected cells.

In some embodiments, a bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known to the skilled artisan.

In some embodiments, prior to applying the membrane, a stent may be polished, cleaned, and/or primed as is known in the art. A stent may be further polished, for example, with an abrasive or by electropolishing. A stent may be cleaned by inserting the stent into various solvents, degreasers, and cleansers to remove any debris, residues, or unwanted materials from the stent surfaces. Optionally, a primer coating may be applied to the stent prior to application of the membrane covering or coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure.

In some embodiments, a stent may include a single flange, two asymmetrically shaped flanges, or may entirely lack flanges and instead have a uniform or substantially uniform lumen diameter along the entire length of the stent. In some embodiments, a stent may comprise a proximal tube portion, a distal tube portion, a central tube portion disposed between the proximal tube portion and the distal tube portion, such that the stent forms a continuous structure having a substantially uniform inner diameter and outer diameter throughout. A stent may include a uniform lumen diameter along the length of the stent but include slightly flared proximal and/or distal ends. The central body portion may smoothly transition to a flange or flare, or alternatively, may progressively step up in lumen diameter to a flange or flare.

Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of antegrade and retrograde migration. Preferably, the flanges are sized and shaped to accommodate the vessel or organ of implantation. For example, stents destined for lower esophageal implantation may have differently shaped and sized flanges compared to a stent designed for upper esophageal implantation. Further, the flanges may be atraumatically shaped to reduce incidence of tissue perforation and overgrowth. For example, the absolute ends of the flanges may curve or bend inward toward the stent lumen to minimize tissue damage at or near the stent ends. In certain embodiments, a stent may include other design elements configured to secure the stent at the site of implantation. For example, in certain embodiments, a stent may include anchors, hooks, or barbs that will anchor the stent to the internal wall of the targeted body lumen. In other embodiments, the stent may be sutured to the site of implantation at one or more portions of the stent structure.

In some embodiments, a stent may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of the wire. In some embodiments, a stent may include four radiopaque markers with two markers affixed to a first flange and two to a second flange. Optionally, radiopacity may be added to a stent through covering (also referred to as coating) processes such as sputtering, plating, or co-drawing gold or similar heavy metals onto the stent. Radiopacity may also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate. Additional methods are contemplated, including but not limited to, use of palladium or a nitinol wire with a platinum core, such as the DFT® wire available from Fort Wayne Metals, Fort Wayne, Ind.

It is preferable that radiopaque markers be added after the wire profile reduction electropolishing bath occurs so as to prevent damaging the radiopaque markers, if, for example, in the form of radiopaque bands. For example, radiopaque bands may be crimped onto the stent after the wire profile reduction electropolishing bath. Alternatively, radiopaque markers may be pushed out from the area subjected to the wire profile reduction electropolishing bath. Alternately, radiopaque markers may be masked from the area subjected to the wire profile reduction electropolishing bath.

In some embodiments, a stent may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible materials, such as for example, stainless steel, suture materials or other polymeric materials such as polyethylene, ultra-high molecular weight polyethylene, polyester, nylon, or the like. Optionally, the lasso may be coated with a material, such as polytetrafluoroethylene, to reduce frictional interactions of the lasso with surrounding tissue.

In some embodiments, stents may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents are often used in vessels that are subject to changes in shape and/or changes in position, such as those of the peripheral and gastrointestinal systems. Peripheral vessels regularly change shape as the vessels experience trauma from external sources (e.g, impacts to arms, legs, etc.); and many gastrointestinal vessels naturally change shape as peristaltic motion advances food through the digestive tract.

One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization of the lumen as well as working channels through which devices and instruments may be delivered to the site of implantation. A fluoroscope also provides visualization of the patient anatomy to aid in placement of an implantable device, particularly in the gastrointestinal system.

Stents according to the present disclosure may be formed by any suitable method as is known in the art. In certain embodiments, stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments or wires may be of various cross-sectional shapes. For example, the filaments or wires may be flat in shape or may have a circular-shaped cross-section. The filaments or wires may have any suitable initial diameter, such as for example, from about 0.10 to about 0.30 mm.

In some embodiments, stents may be formed from metallic or polymeric sheets or tubular blanks. For example, a stent framework comprising a selected pattern of struts defining a plurality of cells or interstices may be fabricated by subjecting a metallic or polymeric sheet or tubular blank to laser cutting, chemical etching, high-pressure water etching, mechanical cutting, cold stamping, and/or electro discharge machining. After obtaining a sheet of cut, etched or machined material with the appropriate strut pattern, the sheet may be rolled into a tubular shape to form the stent framework. The stent framework may also be machined from a tubular blank, thereby eliminating the need for a rolling step.

In some embodiments, a stent may be made from any suitable biocompatible material(s). For example, a stent may include materials such as shape memory alloys, stainless steel, nitinol, MP35N, gold, tantalum, platinum or platinum iridium, niobium, tungsten, Iconel® (available from Special Metals Corporation, Huntington, W. Va.), ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

In some embodiments, a stent may be fabricated to any suitable dimensions. A stent having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. For example, a stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

A stent according to the present disclosure may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., Evolution™ Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

From the foregoing, the discovery of methods and apparatuses of stents with likely reduced rates of tissue perforation are achieved by various methods and apparatus, including but not limited to, reducing the profile one or more portions of a stent using a wire profile reduction electropolishing bath and/or other wire profile reduction means. It can be seen that the embodiments illustrated and equivalents thereof as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein may be applied and configured to any stent and equivalents.

Those of skill in the art will appreciate that embodiments not expressly illustrated herein may be practiced within the scope of the present discovery, including that features described herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages described above are not necessarily the only advantages of the discovery, and it is not necessarily expected that all of the described advantages will be achieved with every embodiment of the discovery.

What is claimed is:

1. A method of manufacturing a reduced wire profile stent comprising:
    providing a non-welded stent comprising a wire braided or woven into a tubular body having a proximal tube portion, a distal tube portion, a central tube portion disposed between the proximal tube portion and the distal tube portion, and a lumen extending between the proximal tube portion and the distal tube portion, wherein at least one of the proximal or distal tube portions of the tubular body terminates in crowns, the crowns of the tubular body comprising a wire first portion, where the wire first portion and the central tube portion of the tubular body each has a constant circular initial wire profile;
    bathing the wire first portion in a first wire profile reduction solution; and
    applying a first electropolishing voltage to the first wire profile reduction solution bath to reduce the profile of the wire first portion and form a first reduced wire profile stent, where the central tube portion retains the initial wire profile, and the wire first portion has a constant circular wire profile smaller than the initial wire profile.

2. The method of claim 1, further comprising:
    rinsing the first reduced wire profile stent of the first wire profile reduction solution.

3. The method of claim 2, wherein the rinsing the first reduced wire profile stent of the first wire profile reduction solution further comprises rinsing the first reduced wire profile stent with deionized water.

4. The method of claim 1, wherein a second portion of the first tubular body is masked while bathing the wire first portion of the first tubular body in the first wire profile reduction solution.

5. The method of claim 1, further comprising:
    bathing a second portion of the first reduced wire profile stent in a second wire profile reduction solution; and
    applying a second electropolishing voltage to the second wire profile reduction solution bath to reduce the profile of the second portion of the first reduced wire profile stent;
    wherein the second portion of the first reduced wire profile stent is the same or different from the wire first portion of the first tubular body, wherein the first wire profile reduction solution is the same or different from the second wire profile reduction solution, and wherein the first electropolishing voltage is the same or different from the second electropolishing voltage.

6. The method of claim 1, wherein the first wire profile reduction solution comprises at least one of perchloric acid, ethanol, butyl cellusolve, water, methanol, acetic acid, hydrofluoric acid, nitric acid, sulphuric acid, orthophosphoric acid, glacial acetic acid, chromium trioxide, hydrochloric acid, and glycerin.

7. The method of claim 1, wherein the applying the first electropolishing voltage to the first wire profile reduction solution bath to reduce the profile of the wire first portion occurs for about 1-5 minutes.

8. The method of claim 1, wherein the first electropolishing voltage is about 3-15 volts.

9. The method of claim 1, further comprising bringing the first wire profile reduction solution to a temperature of at least one of about room temperature or about −30° Celsius.

\* \* \* \* \*